United States Patent [19]
Li et al.

[11] Patent Number: 5,914,310
[45] Date of Patent: Jun. 22, 1999

[54] AMPHOTERIC SURFACTANTS HAVING MULTIPLE HYDROPHOBIC AND HYDROPHILIC GROUPS

[75] Inventors: Ji Li, East Windsor; Manilal Dahanayake, Princeton Junction; Robert Lee Reierson, Cranbury; David James Tracy, Plainsboro, all of N.J.

[73] Assignee: Rhodia Inc., Cranbury, N.J.

[21] Appl. No.: 08/902,926

[22] Filed: Jul. 30, 1997

Related U.S. Application Data

[63] Continuation of application No. 08/488,389, Jun. 7, 1995, abandoned, which is a continuation of application No. 08/292,993, Oct. 19, 1994.

[51] Int. Cl.[6] .................................. C11D 1/88; C11D 1/94
[52] U.S. Cl. ..................... 510/499; 562/561; 562/565; 554/58; 554/59; 510/535; 510/501; 510/502; 510/506; 510/433
[58] Field of Search ...................... 562/561, 565; 252/546; 554/58, 59; 510/535, 501, 502, 506, 433

[56] References Cited

U.S. PATENT DOCUMENTS

| | | | |
|---|---|---|---|
| 3,024,277 | 3/1962 | Hotten | 260/534 |
| 3,578,697 | 5/1971 | Marans | 260/465.4 |
| 4,904,719 | 2/1990 | Michel | 524/238 |
| 4,917,993 | 4/1990 | Mukunoki et al. | 430/523 |
| 5,160,450 | 11/1992 | Okahara et al. | 252/174.21 |
| 5,250,702 | 10/1993 | Kondo et al. | 548/542 |
| 5,312,617 | 5/1994 | Unger et al. | 424/9 |

OTHER PUBLICATIONS

*Derwent World Patent Index*, Week 9523. (Derwent Publications, Ltd., London, G.B.) Class A97, AN95–176476, Abstract of RO–B–108,563 (SC Verachim, SA) Jun. 30, 1994.

*Derwent World Patent Index*, Week 9005 (Derwent Publications, Ltd., London, G. B.) Class A26, AN90–030996, Abstract of EP–A–344334 (Wacker Chem. GMBH) Dec. 6, 1989, Counter–Part of U.S.4,904,719.

European Search Report in EP95 40 1881, The European Counter–Part of USSN 08/292,993.

Menger et al. J. Org. Chem, 1993 no month available, 58 pp. 1909–1916.

*Primary Examiner*—Paul Lieberman
*Assistant Examiner*—Charles Boyer
*Attorney, Agent, or Firm*—John Daniel Wood; Craig M. Bell; Paul J. Juettner

[57] ABSTRACT

According to the invention, an improved class of amphoteric surfactant having improved surfactant properties characterized as mild and environmentally safe has been provided comprising compounds of the formula:

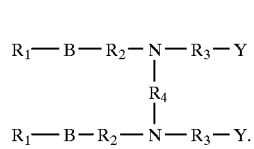

I

The amphoteric surfactant of the subject invention have at least two hydrophobic moieties and at least two hydrophilic groups per molecule and are useful as emulsifiers, detergents, dispersants and solubilizing agents.

19 Claims, No Drawings

AMPHOTERIC SURFACTANTS HAVING MULTIPLE HYDROPHOBIC AND HYDROPHILIC GROUPS

This application is a continuation of application Ser. No. 08/488,389, filed Jun. 7, 1995, now abandoned, which is a continuation of application Ser. No. 08/292,993 filed Oct. 19, 1994.

This invention relates to a novel group of amphoteric surfactants having at least two hydrophobic moieties and at least two hydrophilic groups per molecule useful as emulsifiers, detergents, dispersants, hydrotropes, wetting agents, corrosion inhibitors and solubilizing agents.

BACKGROUND OF THE INVENTION

Surfactants are well known materials which can be generally described as having a hydrophobic moiety and a hydrophilic group per molecule. A wide variety of these materials are known and are classified as anionic, cationic, nonionic and amphoteric. They are well known to be useful as emulsifiers, detergents, dispersants and solubilizing agents in the fields of cosmetics, textile treatment, industrial and personal cleaning preparations, corrosion inhibitors and the like.

In many surfactant containing compositions, such as personal cleaning preparations, mildness is a sought after characteristic. The amphoteric surfactants are particularly important in fulfilling that need. Amphoteric surfactants are compounds uniquely structured to function as cationic surfactants at acid pH and anionic surfactants at alkaline pH. At neutral pH, the amphoteric surfactants are neutral thus accounting for their mildness. These compounds are well known and some of these are shown in U.S. Pat. Nos. 3,941,817; 4,705,843; 2,781,354 and 2,773068 which are illustrative. Amphoteric surfactants are also known to be biodegradable, hence are ecologically compatible.

Surfactants generally are compounds having one hydrophilic group and one hydrophobic moiety. Recently, a group of compounds having two hydrophobic moieties and two hydrophilic groups have been introduced. These have become known as "Gemini surfactants" in the literature [(*Chemtech*, March 1993, pp 30–33, -), and *J.American Chemical Soc.*, 115. 10083–10090, (1993] and the references cited therein. Since their introduction, cationic and anionic "Gemini surfactants" have been disclosed. Other surfactant compounds having two hydrophilic groups and two hydrophobic moieties have been disclosed but not referred to as Gemini surfactants.

Due to the need for new and more effective and efficient surfactants, as well as the need for mild surfactants which are biologically compatible in an ecologically sensitive environment, effort has been made to develop a new class of compounds, which demonstrate improved surface-active properties that are further characterized as mild, and environmentally benign.

SUMMARY OF THE INVENTION

According to the invention, an improved class of amphoteric surfactants having improved surfactant properties characterized as mild and environmentally benign has been provided comprising compounds of the formula:

I

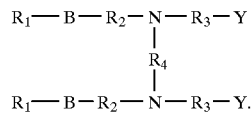

wherein $R_1$ can independently be $C_5$ to about $C_{22}$ alkyl or the hydroxy substituted or perfluorinated derivatives thereof, $R_2$ can independently be $C_1$ to about $C_{12}$ alkylene or hydroxy substituted alkylene; B can be an amide group [—C(O)N($R_5$)— or —N($R_5$)C(O)—], a carboxyl group [—C(O)—O— or —OC(O)—] or a polyether group [—O($R_6$—O)$_x$—], wherein $R_5$ independently represents lower alkyl or hydroxy substituted alkyl from 1 to about 4 carbons or hydrogen and $R_6$ independently represents about $C_2$ to about $C_4$ alkyl with x being a number between 1 and 20; $R_3$ can independently be $C_1$ to about $C_{10}$ alkylene and the hydroxy substituted derivatives thereof or $R_7$—D—$R_7$ or a polyether group [—O($R_6$—O)$_x$—], wherein $R_6$ is as defined hereinbefore and $R_7$ can independently be $C_1$ to about $C_6$ alkylene and the hydroxy substituted derivatives thereof or $R_7$—D—$R_7$, or a polyether group and D represents —O—, —S— or —N($R_8$)— wherein $R_8$ independently represents $C_1$ to about $C_{12}$ alkyl and the hydroxy substituted derivatives thereof or hydrogen; $R_4$ can independently be alkylene or alkylaryl of 1 to about 10 carbon atoms and the hydroxy substituted derivatives thereof or $R_9$—$D_1$—$R_9$ wherein $R_9$ can independently be alkylene of from 1 to about 6 carbon atoms and the hydroxy substituted derivatives thereof as well as aryl illustrated by phenylene, diphenylene and sulphonyldiphenylene, and $D_1$ represents —O—, —S—, —SO$_2$—, a carbonyl group, a polyether group [—O($R_6$—O)$_x$—], —($R_{10}$)$_y$[N($R_{10}$)]$_z$— or aryl wherein $R_{10}$ represents alkyl of from 1 to about 12 carbon atoms and the hydroxy substituted derivatives thereof or hydrogen, $R_6$ being as defined hereinbefore with x being a number between 1 and 20 and y and z are independently numbers from 1 to about 4; and Y independently represents —SO$_3$H, —OSO$_3$H, —OP(O) (OH)$_2$, —P(O) (OH)$_2$, —COOH, —CO$_2$—$C_6H_4$—SO$_3$H and salts thereof.

Preferably, $R_1$ is alkyl or perfluoroalkyl of from about $C_6$ to about $C_{18}$ carbon atoms. $R_2$ is preferably alkylene of from about $C_2$ to about $C_6$ carbon atoms. B is preferably an amide group. Preferably, $R_3$ is independently lower alkylene of from 1 to about 4 carbon atoms and the hydroxy substituted derivatives thereof. $R_4$ is preferably lower alkylene and the hydroxy substituted derivatives thereof of from 1 to 10 carbon atoms. Y is preferably carboxy, sulfate, phosphate and salts thereof.

When compared to the corresponding conventional amphoteric surfactants of the lauryl amphopropionate and coco amphosulfonate types, the novel compound of the invention show two unexpected surface active properties; unusually low critical micelle concentration (CMC) and pC-20 values in aqueous media. These properties are a measure of the tendency of the surfactant to form micelles and adsorb at the interface respectfully, and consequently, to reduce surface tension.

The salts of Formula I can be an alkali metal salt (Na, K), an alkaline earth metal salt (Mg, Ca), an ammonium salt, or an organic base salt. The organic base salt can be illustrated by monoethanolamine, diethanolamine, triethanolamine, triethylamine, trimethylamine, N-hydroxyethyl morpholine and the like.

Preferably, the compounds of the present invention comprise:

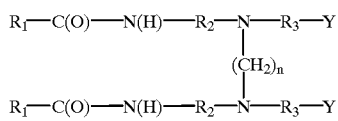

II.

more particularly, the compounds of the invention comprise:

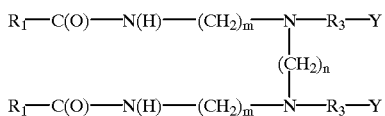

III.

wherein $R_1$, $R_2$, $R_3$, and Y are as defined hereinbefore, n equals a number of between about 2 to about 10, and m equals a number between about 2 and about 10.

Representative compounds within the invention include:

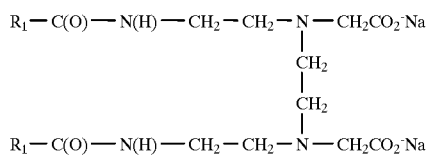

IV.

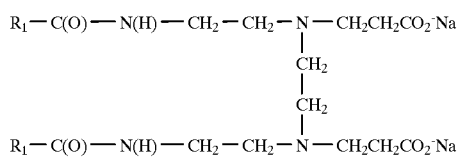

V.

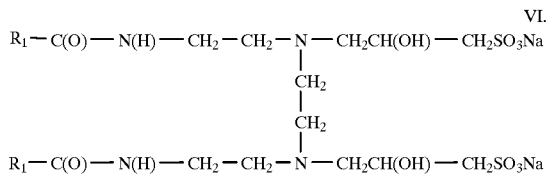

VI.

In addition to new compounds, the invention also provides novel methods of preparing the same as well as new synergistic compositions when blended with other surfactants.

DETAILED DESCRIPTION OF THE INVENTION

In the compounds of the above formulae, $R_1$ is derived from fatty acids from natural or synthetic sources and generally will contain mixtures of different carbon chain length radicals within the chain length ranges defined above. $R_1$ can be a mixture of saturated and unsaturated aliphatic radicals. The natural sources can be illustrated by coconut oil or similar natural oil sources such as palm kernel oil, palm oil, soya oil, rapeseed oil, castor oil or animal fat sources such as herring oil and beef tallow. Each R from natural sources can be a mixture of alkyl radicals containing from about 5 to about 22 carbon atoms. In a more preferred material, the mixture of alkyl radicals can be derived from a saturated portion of coconut oil or similar natural vegetable oil. In the case of coconut oil fatty acid, each R ranges from about 6 to about 18 carbon atoms. These ranges are given as covering about 90% of the R groups, i.e., carbon chains, in the compound. Since these R groups are derived from natural sources, they can contain small amounts of other carbon chains. Illustrative of the fatty acids in these oils are caprylic($C_8$), capric(10), lauric (12), myristic(14), palmitic(16), stearic (18), oleic (18, monounsaturated), linoleic (18, diunsaturated), linolenic (18, triunsaturated), ricinoleic (18, monounsaturated), arachidic (20), gadolic(20, monounsaturated), behenic (22) and erucic(22). These fatty acids can be used Per se, as concentrated cuts or as fractionations of natural source acids. The even numbered acids are given as illustrative though the odd numbered fatty acids can also be used. In addition, amphoterics, based on single carboxylic acids, e.g., lauric acid, or other cuts, as suited for the particular application, may be used. Examples of useful acids derived from synthetic sources are 2-ethylhexanoic acid, pelargonic acid and the like.

While the compounds of the present invention can be prepared by a variety of synthetic routes, it has been found that they can be produced particularly effectively by a novel process which utilizes a polyamine reactant having at least four amino groups of which two are terminal primary amines. The preferred polyamine can be illustrated by triethylene tetramine (TETA). Other polyamines such as tetraethylenepentamine and others can also be used. The amine reactant can be defined by the structure:

VII. $H_2NCH_2CH_2NH-R_4-NHCH_2CH_2NH_2$ wherein $R_4$ is generally alkyl or aminoalkyl. The improved method of the invention will be illustrated with TETA but this is not intended to limit the invention to that starting material.

TETA is reacted with a fatty acid or ester or triglyceride to form a bisimidazoline as per the equation:

VIII.

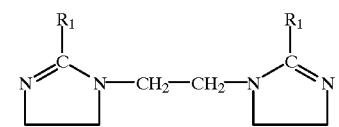

This compound can be generically defined by the structure:

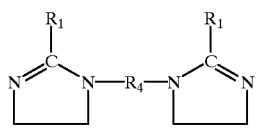

IX.

The fatty acids, esters or triglycerides thereof can be reacted with the polyamines at temperatures ranging from about 150° to 250° C. with continuous removal of the resulting condensate ($H_2O$). The process can be carried out with excess amine, with or without a catalyst, at atmospheric, reduced or super atmospheric pressure.

The bisimidazoline compound, when hydrolyzed under basic pH conditions will selectively form a bisamidoamine compound of Formula X:

X. $R_1C(O)HNCH_2CH_2NHCH_2CH_2NHCH_2CH_2NH(O)CR_1$

This compound can be generically represented by compounds of the formula:

XI. $R_1C(O)HNCH_2CH_2NH-R_4-NHCH_2CH_2NH(O)CR_1$

The bisamidoamine compound (Compounds of Formula X or XI) can then be reacted with an alkylating agent to prepare the bisamphoteric compounds of the invention as defined in Formula I such as an organic compound with a reactive halogen illustrated by chloroacetic acid, its esters or salts; an active vinyl compound, which undergoes Michael addition, illustrated by methyl acrylate or sodium vinyl sulfonate; or electrophiles such as propane sultone or sodium, 3-chloro-2-hydroxypropyl sulfonate and the like.

For alkylation conditions and commonly used alkylating agents, see Amphoteric Surfactants Vol. 12, Ed. B. R. Bluestein and C. L. Hilton, *Surfactant Science Series* 1982, pg. 17 and references cited therein, the disclosures of which are incorporated herein by reference.

A second mode of synthesis from ethylenediamine and a fatty acid can be shown by the following equation:

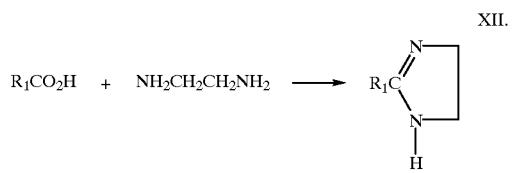

XII.

The fatty acids or esters or triglycerides thereof can be reacted with α,β-diamines at temperatures ranging from about 150° to 250° C. with continuous removal of the resulting condensate ($H_2O$). The process can be carried out with excess amine, with or without a catalyst, at atmospheric, reduced or super atmospheric pressure.

The imidazoline as represented by Formula XII can then be reacted with any difunctional compound that will join two of the imidazoline rings to form the bisimidazoline compound as represented by Formula X. These can be illustrated by any reactive dihalide, e.g., alpha, omega-dihalobutane, alpha, beta-dihaloethane, alpha, alpha'-dihaloparaxylene, diglycidyl ethers, diepoxides as w ell as epihalohydrins such as epichlorohydrin and the like.

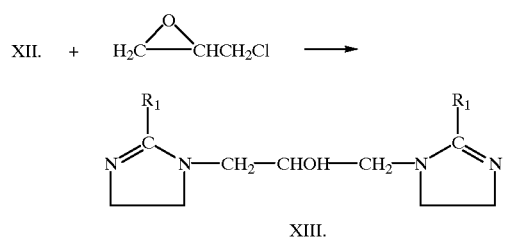

XIII.

In addition to the groups above in connection with the polyamine, $R_4$ can be illustrated by hydroxy substituted alkyl such as —$CH_2CHOHCH_2$; an ether such as —$CH_2CH_2OCH_2CH_2$ or an alkylarylalkyl such as —$CH_2C_6H_4CH_2$—.

For reaction conditions generally, see JACS 67, 1581 (1945); U.S. Pat. Nos. 1,790,042; 1,845,403; JCS 1666 (1931), the disclosures of which are incorporated herein by reference.

The bisimidazoline compound represented by Formula XIII like the bisimidazoline compound represented by Formula VIII as discussed hereinbefore, when hydrolyzed under basic pH conditions will form the amidoamine compound as represented by Formula XI where $R_4$ is —$CH_2CH(OH)CH_2$— which can be reacted with an alkylating agent to form the bisamphoteric compounds represented by Formula I.

The surfactants of the invention can be used alone as the essential hydrotrope component.

It has also been unexpectedly found that blends of the compounds of the invention as defined by the formula

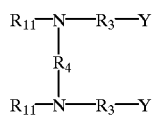

wherein $R_1l$ can independently be alkyl or hydroxy alkyl of from 5 to 22 carbons or $R_1$—B—$R_2$ wherein $R_1$, $R_2$, $R_3$, and $R_4$ are as defined hereinbefore with certain conventional well known anionic, nonionic, cationic and amphoteric surfactants provide synergistic results that can be demonstrated in relation to critical micelle concentration and surface tension reducing ability.

Examples of the nonionic surfactants used herein include fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, an alkylpyrrolidone, glucamides, alkylpolyglucosides, mono- and dialkanol amides, a polyoxyethylene alcohol mono- or diamides and alkylamine oxides. Examples of the anionic surfactants used herein include fatty acid soaps, ether carboxylic acids and salts thereof, alkane sulfonate salts, α-olefin sulfonate salts, sulfonate salts of higher fatty acid esters, higher alcohol sulfate ester salts, fatty alcohol ether sulfates salts, higher alcohol phosphate ester salts, fatty alcohol ether phosphate ester salts, condensates of higher fatty acids and amino acids, and collagen hydrolysate derivatives. Examples of the cationic surfactants used herein include alkyltrimethylammonium salts, dialkyldimethylammonium salts, alkyldimethylbenzylammonium salts, alkylpyridinium salts, alkylisoquinolinium salts, benzethonium chloride, and acylamino acid type cationic surfactants. Examples of the amphoteric surfactants used herein include amino acid, betaine, sultaine, phosphobetaines, imidazoline type amphoteric surfactants, soybean phospholipid, and yolk lecithin.

In addition to the foregoing surfactants, any of the commonly used auxiliary additives may be added to the surfactants of the invention or blends thereof with other surfactants as disclosed herein. Such auxiliary additives may be suitably chosen for a desired composition and generally include inorganic salts such as Glauber salt and common salt, builders, humectants, solubilizing agents, UV absorbers, softeners, chelating agents, and viscosity modifiers.

The amphoteric surfactants of the present invention exhibiting greater surface tension reduction, low toxicity, and excellent compatibility with other anionic, cationic and nonionic surfactants, and being extremely mild and non-irritating to both eyes and skin as well are adaptable for use in products ranging from cosmetics to industrial applications and are usable wherever amphoteric surfactants have found use.

These products are particularly useful for non-irritating shampoos including baby shampoos, body shampoos including bubble baths, bar soaps, bath gels, hair conditioning gels, lotions, skin creams and lotions, make up removal creams and lotions, liquid detergents, dish detergents and other washing and cosmetic products that contact the skin as well as bleach activators and bleach stabilizers and the like.

In addition, the compounds and compositions of the invention can be used in connection with hard surface cleaners, high electolyte cleaners, emulsion polymerization, liquid and bar soap, laundry and dish detergents, bottle washing, carpet shampoo, water based lubricants, metal cleaning, wax softener, oil well drilling lubricant and the like.

Examples of the present invention are given below by way of illustration and not by way of limitation. All parts and percents are by weight.

EXAMPLE 1

Synthesis of Ethylene bis-laurimidazoline of Formula VIII where $R_1$ is $C_{11}H23$ To a 500 mL, three-necked, round bottom flask equipped with a stirrer, temperature controller, and a Barrett distilling receiver with a condenser on top, was added 46.7 g (0.25 mol) triethylenetetramine hydrate (average 2.1 to 2.2 moles water by Karl Fisher Analysis), 104 g (0.52 mol) lauric acid and 100 mL toluene. The Barrett distilling receiver was filled with toluene. The reaction mixture was gently heated with stirring to reflux (120°–130° C.) and water collection was initiated.

The progress of the reaction was followed by monitoring the amount of water collected as the toluene azeotrope. The first 20 mL which was collected in the first three hours of the reflux period indicated that the reaction was 70% complete.

The reaction temperature was slowly raised to 160°–180° C. during the 12 to 16th hour of reaction by stripping the reactor-contained toluene through the Barrett distillation receiver. The progress of the reaction was also determined by gas chromatography. The disappearance of the peak corresponding to the diamide indicated completion of the condensation reaction.

After 16 hours of reaction, the reaction was stopped, as 27.2 mL (99% of the theoretical 28 mL) of water had been collected. Gas chromatography showed that the 126 grams of product obtained contained greater than 96% of the desired ethylene bis-laurimidazoline (VIII).

The product was recrystallized from $CHCl_3$ for structure characterization and identification. The $^1H$ and $^{13}C$ NMR, IR, and Mass Spectra were recorded and the results agreed with the postulated structure.

EXAMPLE 2

Synthesis of N,N'-bis(2-lauramidoethyl ethylenediamine of Formula X wherein $R_1$ is $C_{11}H_{23}$ To a 100 mL three-necked round bottom flask equipped with magnetic stirrer-bar, temperature control, a condenser and a pH probe connected with a readout, was added a solution of 0.2 g of NaOH in 2 mL water and 4.74 g (10 mmol) of ethylene bis-laurimidazoline prepared by the process in Example 1. The reaction mixture was then stirred, heated and maintained at 85–95° C. for 6–8 hours until the pH value of the reaction mixture remained unchanged. Analysis by gas chromatography indicated less than 5% of the starting material (some of the starting material shown by GC is caused by cyclization of the compound of Formula IX in GC injection port). The reaction was stopped at this point to avoid further hydrolysis of the desired bisamidoamine compound of Formula X. The mixture was cooled to 60° C. and diluted with 2 mL tetrahydrofuran. The crude product precipitated as a white solid as the liquid cooled to room temperature. Recrystallization from 4 mL of fresh tetrahydrofuran produced 4.1 g (80% yield) of the N,N' bis (2-lauramidoethyl) ethylenediamine, mp. 110–112° C. The $^1H$ and $^{13}C$ NMR, DEPT$^{13}C$ NMR, IR and Mass Spectra were recorded and agreed with the proposed structure.

EXAMPLE 3

Synthesis of the N,N'-bis(2-lauramidoethyl) ethylenediamine-N,N' di(sodium propionate), compound of Formula V wherein $R_1$ is $C_{11}H_{23}$ To a 250 mL three-necked, round bottom flask equipped with a magnetic stirring bar, temperature control, and a condenser was added 5.9 g (10 mmol) of N,N'-bis(2-lauramidoethyl) ethylenediamine of Example 2 (greater than 98% purity) and 8.6 g (100 mmol) of methyl acrylate. The reaction mixture was then refluxed at 80° C. for 13 hours with stirring. After stripping out excess methyl acrylate under vacuum, 6.35 g (100% yield) of white waxy solid product was obtained. Gas chromatography showed that the waxy solid contained more than 98% of the desired di-(methyl ester) of the title compound which was characterized by $^1H$ and $^{13}C$ NMR.

To another 250 mL, three necked, round bottom flask equipped with a magnetic stirrer bar and temperature control, was added 0.7 g NaOH in 23 mL of water. The reaction mixture was heated to 45° to 55° C. At this temperature, 5.6 g of the white, waxy dimethyl ester product obtained above was added in one portion. The reaction mixture was stirred at 45° to 55° C. for 5 to 6 hours.

After completion of the hydrolysis, the contents were transferred to a beaker which was then placed in a heated water bath. Evaporation of the water left 5.7 grams of the amphoteric surfactant of the title compound, Formula V, as a white solid. The $^1H$ and $^{13}C$ NMR were recorded and agreed with the proposed structure.

EXAMPLE 4

Synthesis of N,N' bis(2-lauramidoethyl) ethylenediamine-N,N' di(sodium acetate) compound of Formula IV wherein $R_1$ is $C_{11}H_{13}$ To a 500 mL three-necked, round bottom flask equipped with a mechanical stirrer bar, thermometer and a condenser, 28.4 g (300 mmol) of monochloroacetic acid and 200 mL of water were added. The stirred solution was cooled in an ice bath during the dropwise addition of 26.2 g (300 mmol) 50% NaOH to maintain the temperature below 25° C. The ice bath was removed, and 61.5 g (100 mmol) of bisamidoamine of Formula X prepared according to Example 2 and 50 g of isopropyl alcohol was added and the liquor was heated to 75° C. The pH was maintained at 9–10.5 by addition of 21.8 g (270 mmol) 50% NaOH at 75° C. over the 5 hour reaction period. The reaction mixture was then heated to 85° C. and 42 mL of IPA/water was distilled out and replaced with 42 ml of water. The reaction was run another 12 hours at 90° C., until the reaction was complete as indicated by the free to total chloride ratio of near unity (>0.99~99% conversion).

The solvent was allowed to evaporate overnight in a crystallizing dish in the hood. Drying was completed in a vacuum oven at 70° C. for 2 hours, to give 74 g of the desired product. (81% of theoretical) The structure was confirmed by the $^{13}C$ NMR spectrum.

EXAMPLE 5

Synthesis of N,N' bis(2-lauramidoethyl) ethylenediamine-N,N'-di(sodium 2-hydroxy-3 propyl sulfonate) compound of Formula VI wherein $R_1$ is $C_{11}H_{23}$ To a 250 mL, three-necked, round-bottom flask equipped with a mechanical stirrer bar, thermometer and a condenser, were added 5.7 g (60 mmol) of sodium metabisulfite, 60 mg of 50% NaOH and 33.9 g of water. The reaction mixture was heated to 50–60° C. and epichlorohydrin (5.55 g, 60 mmol) was added over a period of about an hour. The reaction mixture was then heated with stirring at 60–65° C. for one hour, after which 10.3 g (20 mmol) of the bisamidoamine compound of Formula X prepared according to the process of Example 2, 12 g of isopropyl alcohol and 44 g of water were added. The reaction mixture was heated to reflux, and 4.8 g (60 mmol) of 50% NaOH was added over a period of 3 hours.

About 6 mL of alcohol/water was then distilled out and replaced with 8 mL of water. After heating to reflux for two hours, another 10 mL of water was added and reflux continued for another hour.

The product was evaporated to dryness, extracted with tetrahydrofuran, and the solvent evaporated. Yield: 15 g, 60% yield. Structure confirmed by $^{13}C$ NMR.

EXAMPLE 6

Synthesis of N,N'-bis(2-caprylamidoethyl) ethylendiamine-N,N'-di(sodium propionate) compound of Formula V wherein $R_1$ is $C_7H_{15}$ Preparation of the bisimidazoline compound of Formula VIII wherein $R_1$ is $C_7H_{15}$.

The procedure of Example 1 was repeated using 100 g (0.538 mol) of triethylenetetramine hydrate, 154.9 g (1.076 mol) of octanoic acid and 100 mL of toluene.

Preparation of bisamidoamine compound of Formula X wherein $R_1$ is $C_7H_{15}$.

The procedure of Example 2 was followed using a 500 mL, 3-necked round bottom flask, 145 grams (0.4 mol) of bisimidazoline as prepared above, 4 g of 50% NaOH and 4 mL of water. Reaction time was 4 hours. The product was recrystallized from 80 mL of tetrahydrofuran and 200 mL water. The yield was 80 grams (42% yield) and the structure was confirmed by $^{13}C$ NMR.

Synthesis of amphoteric surfactant compound of Formula V wherein $R_1$ is $C_7H_{15}$ To a 500 mL, four-necked, round bottom flask equipped with a mechanical stirrer, thermometer and condenser was added 64.0 g (0.16 moles) bisamidoamine as prepared above and 62 g of toluene and heated to 75–85° C.

Methyl acrylate (55.4 g, 0.64 mol) was added dropwise over a period of one hour. The reaction temperature was maintained at 80–85° C. for 16 hours. Excess toluene and methyl acrylate were stripped. $^{13}C$ NMR confirmed the desired structure with a product purity of about 90%.

To this crude mixture was added 360 mL of water and 11.2 g (0.14 moles) of 50% NaOH and heated to 93–97° C. Another 11.2 g (0.14 moles) of 50% NaOH was added incrementally to maintain the pH at 9.0–10.0. Total reaction time was six hours. The reaction mixture was placed in an evaporating dish and evaporated to dryness at 60–80° C. and finished in a vacuum oven. The product was extracted in a Soxhlet extractor with tetrahydrofuran for four hours. The product was allowed to air dry to remove tetrahydrofuran, and drying was completed in vacuum oven. Yield 45.5 g, 49.2% yield. The structure was confirmed by $^{13}C$ NMR.

SURFACE PROPERTIES

The surfactants of the invention were measured for critical micelle concentration and their ability to reduce surface tension.

The test methods utilized are described as follows:

Critical Micelle Concentration (CMC)

Aqueous solutions of a surfactant were prepared at varying concentrations. The surface tension at 20° C. was measured by the Wilhelmy plate method and plotted vs. the logarithm of the concentration. The critical micelle concentration was determined as the value at which the slope of the line changed abruptly.

Surface Tension Reducing Ability (gamma CMC)

The surface tension reducing ability was determined from the surface tension at the critical micelle concentration.

Surface tension measurements were made for each of the referenced surfactants, using a Kruss K-12 Tensiometer (plate method). Each experiment was carried out as follows.

Distilled water solutions at different concentrations were prepared for each of the test surfactants in 100 mL amounts. The mixtures were stirred until homogeneous solutions were obtained. The surface tensions of these solutions were then measured.

From the surface tension data, the area/molecule (area) at the interface and efficiency of adsorption were computed by use of the appropriate Gibb's Adsorption Equation:

$$\rho = \frac{-d\gamma}{d\log C_T} / 2.303 RT$$

where

ρ=surface excess concentration (mol/cm$^2$)

dγ=change in surface or interfacial tension of the solvent (dyn·cm$^{-1}$)

R=8.31×10$^7$ erg mol$^{-1}$·K$^{-1}$

C=molar concentration of solution

T=absolute temperature (OK)

pC-20 at the solution /air interface is defined as the negative logarithm of the surfactant concentration required to lower surface tension by 20 dyne/cm.

The results obtained for the surfactants alone are reported in Table 1.

TABLE 1

| SURFACE ACTIVITY | | | | |
|---|---|---|---|---|
| Surfactant | CMC (M) | γ$_{cmc}$ | AREA (Å$^2$) | pC-20 |
| Product of EXAMPLE 3 (C12 PROPIONATE) pH 9.5, 0.1M NaCl | 6.3 × 10$^{-7}$ | 34.0 | 56 | 7.3 |
| Product of EXAMPLE 5 (C12 SULPHONATE) pH 7.0, 0.1M NaCl | 3.5 × 10$^{-6}$ | 29.5 | 53 | 6.7 |
| CONTROL MIRANOL® H2M-SF (Lauroamphodipropionate) pH 9.5, 0.1M NaCl | 4.7 × 10$^{-5}$ | 33.5 | 63 | 5.6 |
| CONTROL MIRANOL® ULTRA (Cocoamphoacetate) pH 6, 0.1M NaCl | 2.0 × 10$^4$ | 26.5 | 63 | 5.4 |

TABLE 1-continued

SURFACE ACTIVITY

| Surfactant | CMC (M) | $\gamma_{cmc}$ | AREA ($\text{Å}^2$) | pC-20 |
|---|---|---|---|---|
| CONTROL RHODAPEX ® ESY (Lauryl Ether Sulfate) pH 6, 0.1M NaCl | $8.0 \times 10^{-5}$ | 30.2 | 42 | 5.0 |
| CONTROL MIRANOL ® CS (Cocamphohydroxypropyl sulphonate) pH 7, 0.1M NaCl | $5.6 \times 10^{-5}$ | 27.0 | 58 | 5.8 |

Hydrotropicity was measured by determining the amount of surfactant needed to clarify a cloudy aqueous solution of 5% sodium hydroxide and 5% surfactant (IGEPAL® CO-630—Nonylphenol ethoxylate—9 moles EO). The results are expressed in weight percent of the aqueous solution. The lower the number, the greater the hydrotropicity. The results show that the product of Example 6 is over 60% more efficient than the conventional surfactant MIRANOL® JEM.

TABLE 2

| SURFACTANT | HYDROTROPICITY (Wt. %) |
|---|---|
| Product of EXAMPLE 6 ($C_8$ PROPIONATE) | 0.3% |
| MIRANOL ® JEM (Sodium Mixed $C_8$ Amphocarboxylate) | 0.8% |

When the surface properties for the amphoteric $C_{12}$ propionate and $C_{12}$ sulfonate compounds of the invention are compared to the corresponding conventional amphoteric laurylamphopropionate and cocoamphosulfonate as shown in Table 1, the novel compounds of the invention show two unexpected surface active properties; unusually low critical micelle concentration (CMC) and pC-20 values in aqueous media. These properties are a measure of the tendency of the surfactant to form micelles, and adsorb at the interface, and consequently, to reduce surface tension, respectively. The values shown in Table 1 demonstrate that the $C_{12}$ propionates and sulfonates are one to two orders of magnitude (or 10 to 100 times) more efficient at reducing surface tension (pC-20) and more than two orders of magnitude (or 100 times) more effective at forming micelles. This unusually high surface activity for these molecules is a result of their unique structure; the presence of two optimally spaced hydrophobic moieties and hydrophilic groups. This molecular structure provides energetically favorable decreases in the free energy of adsorption and micellization through favorable distortion of the water structure, while simultaneously, providing a "closed packed" arrangement at the interface as reflected by the unusually low area per molecule compared to that which would be expected from the molecular dimensions. The area per molecule for the compounds of the invention are less than that of conventional amphoterics having single hydrophilic chains and hydrophobic moieties, based on similar starting materials and about half the molecular weight. The ability of the compounds of the invention to distort water structure through inhibition of crystalline or liquid crystalline phase formation in the bulk phase and at the same time to pack closely on adsorption at the interface is contrary to conventional wisdom. This again demonstrates the uniqueness of the molecular design for these compounds which is very critical to providing, unexpected, exceptional surface and performance properties.

Exceptional surface activity and unique structural features for the compounds of the invention provide two other important performance properties that can have immense practical application in industry. They are hydrotropicity, which is the ability of organic substances to increase the solubility of other, insoluble organic substances in water, and solubilization, the dissolving of water insoluble organic compounds into aqueous surfactant solutions above their critical micelle concentrations. The compounds of the invention, because of their very low CMC values, are efficient solubilizers. This latter property will not only allow the formulation of homogeneous water insoluble materials, but also will enhance the surface activity of other surfactants whose low water solubility restricts their use. These novel surfactants of the invention are far better than comparable conventional surfactants in hydrotroping and solubilizing properties.

Because of their unusually high surface activity coupled with their hydrotropicity and solubilization properties, compounds of this invention will provide exceptionally high performance properties, at very low concentration, in practical applications such as detergency emulsification, solubilization, dispersancy, hydrotropicity, foaming and wetting. Because of their greater surfactant efficiency as indicated by the extremely low CMC and pC-20 values, from ten to 100 times lower concentrations of the compounds of the invention can be used compared to the invention than conventional surfactants, substantially reducing the need for the surfactant component to achieve equivalent results and thus reducing the among of surfactant released into waste treatment facilities. Additionally, since the CMC is the maximum free surfactant concentration (that is, uncomplexed in micelles) under use conditions, this lower level of the active species should result in a much lower level of irritancy, even essentially none, if as is likely, it is below the irritancy threshhold concentration.

SURFACE ACTIVITIES OF MIXTURES

The unusually high surface activity of the amphoteric surface active agents of the invention make them the surfactants of choice in enhancing the surface activity of mixtures containing other conventional significantly less surface active zwitterionic, amphoteric, nonionic and cationic surfactants. The propionate and sulfonate compounds of the invention provide significant, unexpected improvement in the surface activity of blends of these compounds with the above types of surfactants, even when used in very small amounts. The improvement is beyond that which would be estimated from an average of the properties of the components of the surfactant mixture, hence showing positive synergism. The results are shown in Table 3 as follows:

TABLE 3

SURFACE ACTIVITIES of MIXTURES

| PRODUCT OF EXAMPLE 3 (C12 propionate) pH 7, 0.1M NaCL | (M) | $\gamma_{cmc}$ | AREA ($\text{Å}^2$) | pC-20 |
|---|---|---|---|---|
| PLUS MIRANOL ® ULTRA (Cocoamphoacetate) (25/75 mole ratio) | $7.9 \times 10^{-6}$ | 27 | 40 | 6.1 |
| PLUS RHODAPEX ® ESY Lauryl ether Sulfate - 1EO) | $4.8 \times 10^{-6}$ | 26 | 75 | 7.1* |

TABLE 3-continued

SURFACE ACTIVITIES of MIXTURES

| PRODUCT OF EXAMPLE 3<br>(C12 propionate)<br>pH 7, 0.1M NaCL | (M) | $\gamma_{cmc}$ | AREA<br>($\text{Å}^2$) | pC-20 |
|---|---|---|---|---|
| (25/75 mole ratio)<br>PLUS MIRANOL ® H2M-SF<br>(Lauroamphodipropionate)<br>(25/75 mole ratio) pH 9.5 | $2 \times 10^{-6}$ | 32 | 47 | 6.6 |
| CONTROL<br>RHODAPEX ® ESY/<br>MIRANOL ® ULTRA<br>(25/75 mole ratio) pH 6 | $6.5 \times 10^{-5}$ | 25 | 42 | 5.3 |

(*Extrapolated)

As shown in Table 3, the compound of Example 3 ($C_{12}$ propionate) when blended with coco amphoacetate, or the lauryl amphodipropinate comparable conventional amphoterics, at 25/75 molar ratios provided at least a 10 fold improvement in surface activity, as measured by the reduction of CMC and pC-20 compared to the conventional amphoterics alone. Similar order of magnitude improvement in surface activity was obtained for a blend the compound of Example 3 ($C_{12}$ propionate) with a conventional anionic surfactant, laurylethersulfate (RHODAPEX® ESY) at the 25/75 molar ratio. This enhancement of surface activity (CMC AND pC-20) is also one to two orders of magnitude greater than for a mixture of corresponding conventional surfactants, i.e., RHODAPEX® ESY and MIRANOL® ULTRA. This property of enhancement of surface activity and solubilization of blends when used in low concentrations can have wide applicability in industrial, personal care and pharmaceutical applications. The use of the compounds of the invention in combination with conventional surfactants can provide improved performance for blends even at significantly lower concentrations which is very desirable for both economic and environmental reasons.

The product of the invention was evaluated for mildness by an In-Vitro Ocular Irritation (Eytex) study. The product of Example 3 gave an Eytex Draize Equivalent of 9.7. This corresponds to minimal irritation.

The product of Example 3 was also tested in combination with RHODAPEX® ESY. The results indicate that the irritancy of RHODAPEX® ESY was reduced from moderate irritant to minimal/mild when combined with the product of Example 3.

Eytex Draize Equivalent (EDE)

0–15 Minimal

15–19 Minimal/Mild

19–22 Mild

22–25 Mild/Moderate

25–33 Moderate

TABLE 4

Eytex Draize Equivalent (EDE)

| AMOUNT | SAMPLE IDENTIFICATION | EDE |
|---|---|---|
| 10.0% | Product Example 3 | 9.7 |
| 2.5% | Product Example 3 | 21.8 |
| 7.5% | RHODAPEX ® ESY | |
| 5.0% | Product Example 3 | 19.6 |

TABLE 4-continued

Eytex Draize Equivalent (EDE)

| AMOUNT | SAMPLE IDENTIFICATION | EDE |
|---|---|---|
| 5.0% | RHODAPEX ® ESY | |
| 7.5% | Product Example 3 | 18.5 |
| 2.5% | RHODAPEX ® ESY | |
| 10.0% | RHODAPEX ® ESY | 27.1 |

By virtue of the properties discussed above, the surfactants of the invention can be combined with other, conventional surfactants in very small amounts to dramatically improve surface activity, and solubility of blends and, thereby, have wide industrial applicability in significantly improving performance properties such as detergency, emulsification, wetting, dispersancy and solubilization. Further, this property of significantly lowering CMC and pC-20 values in mixtures containing conventional surfactants should provide irritancy mitigating properties when used in combination with other more irritating surfactants, polymers and/or additives.

Mixtures were evaluated for improvement in foam height and wetting ability. Blends of the compounds of the invention with some conventional surfactants showed significant improvement as shown using the following tests.

Ross Miles Foam Height

The product was evaluated as a foaming agent using the Ross Miles Foam Height Test as outlined in ASTM method D1173. The foam was evaluated and the results were recorded.

DRAVES WETTING TEST

The Draves Wetting Test is conducted according to ASTM D 2281-68. A 500 mL surfactant solution containing 0.1% by weight of the test surfactant was prepared. The resulting aqueous solution was poured into 500 mL graduate cylinder and 5 g of 100% cotton yarn weighted with 3 g hook was dropped into the cylinder. The time required for the yarn to sink to the bottom of cylinder was reported as Drave Wetting Time.

The following results were obtained:

TABLE 5

Ross Miles Foam Height

| Product of EXAMPLE 3<br>($C_{12}$ Propionate)<br>0.1 wt % Sol., pH 7 | Ross Miles Foam Height<br>(mm, 0 to 5 min.) |
|---|---|
| BLENDED WITH MIRANOL ® H2M-SF<br>WT. RATIO | |
| 100/0 | 117 → 106 |
| 75/25 | 123 → 123 |
| 50/50 | 136 → 136 |
| 25/75 | 145 → 145 |
| 0/100 | 133 → 133 |

TABLE 6

Draves Wetting Time

| Product of EXAMPLE 3 (C$_{12}$ Propionate) 0.1 wt % Sol., pH 7 | Draves Wetting Time (sec) |
|---|---|
| BLENDED WITH MIRANOL ® H2M-SF WT. RATIO | |
| 100/0 | >300 |
| 75/25 | 133 |
| 50/50 | 116 |
| 25/75 | 81 |
| 0/100 | 140 |

TABLE 7

Draves Wetting Time

| Product of EXAMPLE 3 (C$_{12}$ Propionate) 0.1 wt % Sol., pH 7 | Draves Wetting Time (sec) |
|---|---|
| BLENDED WITH IGEPAL ® CO-430 WT. RATIO | |
| 66/36 | 36.2 |
| 46/54 | 26.0 |
| 37/63 | 33.5 |
| 0/100 | >300 |

As used herein RHODAPEX® ESY is a sodium laurylether sulfate (1 EO); MIRANOL® H2M-SF is a salt free disodium lauroamphodipropionate; MIRANOL® CS is a sodium cocoamphohydroxypropyl sulphonate of the formula (Coco)—C(O) NHCH$_2$CH$_2$N (CH$_2$CH$_2$OH) CH$_2$CH (OH) CH$_2$SO$_3$Na; and MIRANOL® ULTRA is a cocoamphoacetate of the formula (Coco)-C(O) NHCH$_2$CH$_2$N (CH$_2$CH$_2$OH) CH$_2$CO$_2$Na.

MIRANOL® CS, MIRANOL® H2M-SF, MIRANOL® JEM AND MIRANOL® ULTRA are amphoteric surfactants and RHODAPEX® ESY is an anionic surfactant. These materials are available from Rhone-Poulenc Specialty Chemicals Co.

Although the subject invention has been described with respect to a preferred embodiment, it will be readily apparent to those skilled in the art to which the invention pertains that changes and modifications may be made thereto without departing from the spirit or scope of the subject invention as defined by the appended claims.

What is claimed is:

1. A cleaning composition comprising an aqueous solution having a cleanıngly effective amount of two or more surfactants dissolved therein wherein one of said surfactants comprises compounds of the formula:

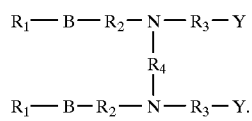

I wherein R$_1$ can independently be C$_5$ to about C$_{22}$ alkyl or hydroxy-substituted or perfluorinated derivatives thereof, R$_2$ can independently be C$_1$ to about C$_{12}$ alkylene or hydroxy-substituted alkylene; B is an amide group of the formula ([—C(O)N(R$_5$)— or —N(R$_5$)C(O)])—R$_1$—C(O) N(R$_5$)—R$_2$—, or a polyether group of the formula (—(O (R$_6$—O)$_x$—)), R$_5$ independently represents (a lower alkyl or hydroxy substituted alkyl of 1 to 4 carbons or) hydrogen; (and R$_6$ independently represents about C$_2$ to about C$_4$ alkyl with x being a number between 1 and 20); R$_3$ can independently be C$_1$ to about C$_{10}$ alkylene and the hydroxy-substituted derivatives thereof (or R$_7$—D—R$_7$ or a polyether group (—(O(R$_6$—O)$_x$)) wherein R$_6$ is as defined hereinbefore and R$_7$ can independently be C$_1$ to about C$_6$ alkylene and the hydroxy substituted derivatives thereof and D represents —O—, —S— or —N(R$_8$)— wherein R$_8$ independently represents C$_1$ to about C$_{12}$ alkyl and the hydroxy-substituted derivatives thereof or hydrogen); R$_4$ can independently be alkylene or alkylaryl of 1 to about 10 carbon atoms and the hydroxy-substituted derivatives thereof (or R$_9$—D$_1$—R$_9$ wherein R$_9$ can independently be alkylene of from 1 to about 6 carbon atoms and the hydroxy-substituted derivatives thereof or aryl, and D$_1$ represents —O—, —S—, —SO$_2$—, a carbonyl group, a polyether group (—O(R$_7$—O)$_x$—), —(R$_{10}$)$_y$[N(R$_{10}$)]$_z$— or aryl wherein R$_{10}$ represents alkyl of from 1 to about 12 carbon atoms and the hydroxy-substituted derivatives thereof or hydrogen, R$_7$ being as defined hereinbefore with x being a number between 1 and 20 and y and z are independently numbers from 1 to about 4); and Y independently represents —SO$_3$H, —OSO$_3$H, —OP(O)(OH)$_2$, —P(O)(OH)$_2$, —COOH, —CO$_2$—C$_6$H$_4$—SO$_3$H and the salts thereof (.) selected from the group consisting of sodium, potassium, ammonium, monoethanolamine, diethanolamine, triethanolamine, triethylamine, trimethylamine, N-hydroxyethyl, morpholine, and mixtures thereof.

2. A cleaning composition of claim 1, wherein the solution is selected from the group consisting of shampoos, soaps, bath gels, hair conditioners, skin creams and lotions, cosmetics, detergents.

3. A cleaning composition of claim 1, wherein R$_1$ is alkyl of from about C$_6$ to about C$_{18}$ carbon atoms.

4. A cleaning composition of claim 1, wherein R$_2$ is alkylene of from about C$_2$ to about C$_6$ carbon atoms.

5. A cleaning composition of claim 1, wherein B is an amide group.

6. A cleaning composition of claim 1, wherein R$_3$ independently is lower alkylene of from 1 to about 4 carbon atoms.

7. A cleaning composition of claim 1, wherein R$_4$ is lower alkylene of from 1 to about 10 carbon atoms.

8. A cleaning composition of claim 1, wherein Y is sulfate, carboxylate, phosphate and salts thereof.

9. A cleaning composition of claim 1, wherein said salt in Formula I is selected from the group consisting of an alkali metal salt, an alkaline earth metal salt, an ammonium salt, and an organic base salt.

10. A cleaning composition as recited in claim 1 in which the other surfactant is selected from the group consisting of an anionic, nonionic, cationic, or amphoteric surfactant and mixtures thereof.

11. A cleaning composition of claim 10, wherein said nonionic surfactant is selected from the group consisting of a fatty acid glycerine ester, a sorbitan fatty acid ester, a sucrose fatty acid ester, a polyglycerine fatty acid ester, a higher alcohol ethylene oxide adduct, a single long chain polyoxyethylene alkyl ether, a polyoxyethylene alkyl allyl ether, a polyoxethylene lanolin alcohol, a polyoxyethylene fatty acid ester, a polyoxyethylene glycerine fatty acid, a polyoxyethylene propylene glycol fatty acid ester, a polyoxyethylene sorbitol fatty acid ester, a polyoxyethylene castor oil or hardened castor oil derivative, a polyoxyethylene lanolin derivative, a polyoxethylene fatty acid amide, a polyoxyethylene alkyl amine, an alkyl pyrrolidone, glucamides, alkylpolyglucosides, a mono or dialkanol amide, a polyoxyethylene alcohol mono or diamide, and an alkylamine oxide.

12. A cleaning composition of claim 10, wherein said anionic surfactant is selected from the group consisting of a fatty acid soap, an ether carboxylic acid and salt thereof, an alkane sulfonate salt, an a-olefin sulfonate salt, a sulfonate salt of a higher fatty acid ester, a higher alcohol sulfate ester salt, fatty alcohol ether sulfate salts, a higher alcohol phosphate ester salt, a fatty alcohol ether phosphate ester salt, a condensate of higher fatty acids and amino acids, and a collagen hydrolysate derivative.

13. A cleaning composition of claim 10, wherein said cationic surfactant is selected from the group consisting of an alkyltrimethylammonium salt, a dialkyldimethylammonium salt, an alkyldimethylbenzylammonium salt, an alkylpyridinium salt, an alkylisoquinolinium salt, benzethonium chloride, and an acylamino acid type cationic surfactant.

14. A cleaning composition of claim 10, wherein said amphoteric surfactant is selected from the group consisting of an amino acid, betaine, sultaine, phosphobetaine, an imidazoline type amphoteric surfactant, soybean phospholipid, and yolk lecithin.

15. A cleaning composition of claim 1, further comprising an auxiliary additive, wherein said auxiliary additive is selected from the group consisting of an inorganic salt, builders, humectants, solubilizing agents, bleach activators and bleach stabilizers uv absorbers, softeners, chelating agents and viscosity modifiers.

16. A process for preparing compounds of the formula:

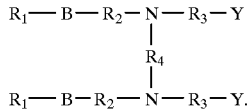
I wherein $R_1$ can independently be $C_5$ to about $C_{22}$ alkyl or hydroxy-substituted or perfluorinated derivatives thereof, $R_2$ represents $C_2$ alkylene or hydroxy-substituted alkylene; B represents an amide group of the formula (—C(O)N($R_5$)), wherein $R_5$ independently represents hydrogen and $R_3$ can independently be $C_1$ to about $C_{10}$ alkylene and the hydroxy-substituted derivatives thereof; $R_4$ can independently be alkylene of 1 to about 10 carbon atoms and the hydroxy-substituted derivatives thereof or $R_9$—$D_1$—$R_9$ wherein $R_9$ can independently be alkylene of from 1 to about 6 carbon atoms and the hydroxy-substituted derivatives thereof as well as aryl, and $D_1$ represents —($R_{10}$)$_y$(N($R_{10}$))$_z$— or aryl wherein $R_{10}$ represents alkyl of from 1 to about 12 carbon atoms and the hydroxy substituted derivatives thereof or hydrogen, and y and z are independently numbers from 1 to about 4; and Y independently represents —$SO_3H$, —$OSO_3H$, —$OP(O)(OH)_2$, —$P(O)(OH)_2$, —$COOH$, —$CO_2$—$C_6H_4$—$SO_3H$ and salts thereof, which comprises:

a. reacting a polyamine of the formula

VII. $H_2NCH_2CH_2NH$—$R_4$—$NHCH_2CH_2NH_2$ wherein $R_4$ is alkyl or aminoalkyl with a fatty acid or ester or triglyceride thereof to form a bisimidazoline of the formula

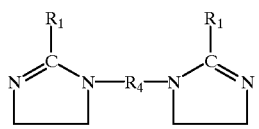
IX.

b. hydrolyzing the bisimidazoline to form a bisamidoamine of the formula

XI. $R_1C(O)HNCH_2CH_2NH$—$R_4$—$NHCH_2CH_2NH(O)CR_1$, and c. alkylating the bisamidoamine to form the compound identified above.

17. A cleaning composition of claim 1, wherein said compound of formula (1) is selected from the group consisting of:

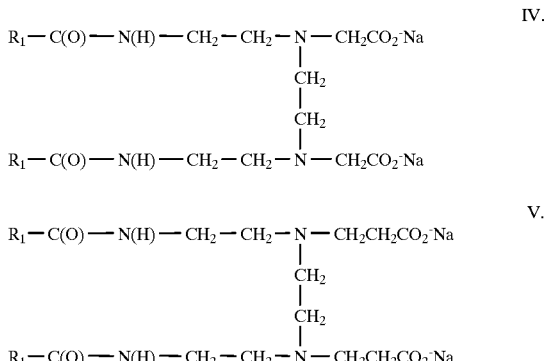

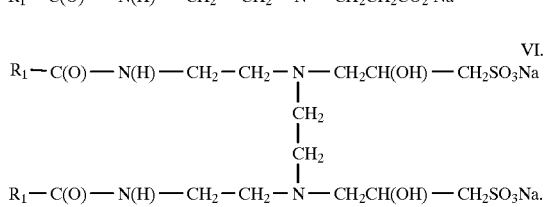

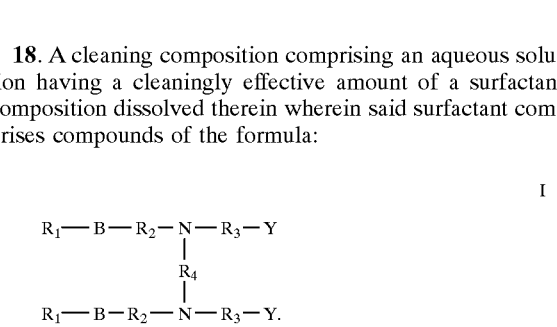

18. A cleaning composition comprising an aqueous solution having a cleaningly effective amount of a surfactant composition dissolved therein wherein said surfactant comprises compounds of the formula:

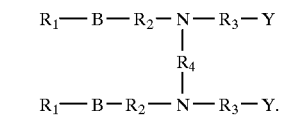
I wherein $R_1$ can independently be $C_1$ to about $C_{22}$ alkyl or hydroxy-substituted or perfluorinated derivatives thereof, $R_2$ can independently be $C_1$ to about $C_{12}$ alkylene or hydroxy-substituted alkylene; B is an amide group of formula $R_1$—C(O)N($R_5$)—$R_2$—, or a polyether group of the formula (—O($R_6$—O)$_x$—), $R_5$ independently represents a lower alkyl or hydroxy-substituted alkyl of 1 to 4 carbons or hydrogen; and $R_6$ independently represents about $C_2$ to about $C_4$ alkyl with x being a number between 1 and 20; $R_3$ can independently be $C_1$ to about $C_{10}$ alkylene and the hydroxy-substituted derivatives thereof or $R_7$—D—$R_7$ or a polyether group (—(O($R_6$—O)$_x$) wherein $R_6$ is as defined hereinbefore and $R_7$ can independently be $C_1$ to about $C_6$ alkylene and the hydroxy-substituted derivatives thereof and D represents —O—, —S— or —N(R$_9$)— wherein R$_8$ independently represents C$_1$ to about C$_{12}$ alkyl and the hydroxy-substituted derivatives thereof or hydrogen; R$_4$ can independently be alkylene or alkylaryl of 1 to about 10 carbon atoms and the hydroxy-substituted derivatives thereof or R$_9$—D$_1$—R$_9$ wherein R$_9$ can independently be alkylene of from 1 to about 6 carbon atoms and the hydroxy-substituted derivatives thereof or aryl, and D$_1$ represents —O—, —S—, —SO$_2$—, a carbonyl group, a polyether group (—O(R$_7$—O)$_x$—), —(R$_{10}$)$_y$[N(R$_{10}$)]$_z$— or aryl wherein R$_{10}$ represents alkyl of from 1 to about 12 carbon atoms and the hydroxy-substituted derivatives thereof or hydrogen, R$_7$ being as defined hereinbefore with x being a number between 1 and 20 and y and z are independently numbers from 1 to about 4; and Y independently represents —SO$_3$h, —OSO$_3$H, —OP(O)(OH)$_2$, —P(O)(OH)$_2$, —COOH, —CO$_2$—C$_6$H$_4$—SO$_3$H and salts thereof together with an auxiliary additive.

19. The cleaning composition of claim 18 wherein said auxiliary additive is selected from the group comprising inorganic salts, a builder, a humectant, a solubilizing agent, bleach activators, bleach stabilizers, emulsion polymerization activators, a UV absorber, a softener, a chelating agent, a viscosity modifier and mixtures thereof.

* * * * *